United States Patent
Cho et al.

(10) Patent No.: US 8,927,455 B2
(45) Date of Patent: Jan. 6, 2015

(54) SINGLE-STEP PRECIPITATION METHOD OF PRODUCING MAGNESIA-ZIRCONIA COMPLEX CARRIER FOR CATALYST FOR OXIDATIVE DEHYDROGENATION OF N-BUTANE, MAGNESIUM ORTHOVANADATE CATALYST SUPPORTED ON MAGNESIA-ZIRCONIA COMPLEX CARRIER, AND METHOD OF PRODUCING N-BUTENE AND 1,3-BUTADIENE USING SAID CATALYST

(71) Applicant: Samsung Total Petrochemicals Co., Ltd., Seosan-si (KR)

(72) Inventors: Young Jin Cho, Seosan-si (KR); Yeon Shick Yoo, Seosan-si (KR); Jin Suk Lee, Seoul (KR); Ho Sik Chang, Daejeon (KR); In Kyu Song, Seoul (KR); Ho Won Lee, Seoul (KR); Jong Kwon Lee, Daejeon (KR)

(73) Assignee: Samsung Total Petrochemicals Co., Ltd., Sesosan-Si (KR)

( * ) Notice: Subject to any disclaimer, the term of this patent is extended or adjusted under 35 U.S.C. 154(b) by 1 day.

(21) Appl. No.: 13/645,189

(22) Filed: Oct. 4, 2012

(65) Prior Publication Data
US 2013/0090509 A1 Apr. 11, 2013

(30) Foreign Application Priority Data
Oct. 6, 2011 (KR) ........................ 10-2011-0101954

(51) Int. Cl.
*B01J 21/04* (2006.01)
*B01J 37/02* (2006.01)
(Continued)

(52) U.S. Cl.
CPC ................. *B01J 21/10* (2013.01); *C07C 11/05* (2013.01); *B01J 37/0201* (2013.01); *B01J 37/036* (2013.01); *C07C 5/48* (2013.01); *B01J 32/00* (2013.01); *B01J 23/22* (2013.01); *C07C 2523/22* (2013.01); *C07C 2523/02* (2013.01); *B01J 37/08* (2013.01); *C07C 2521/06* (2013.01); *C07C 11/167* (2013.01); *Y10S 502/506* (2013.01)
USPC ........... 502/340; 502/349; 502/439; 502/506; 423/608

(58) Field of Classification Search
USPC ........... 502/340, 439, 506; 423/608; 501/104
See application file for complete search history.

(56) References Cited

U.S. PATENT DOCUMENTS

| | | |
|---|---|---|
| 3,303,234 A | 2/1967 | Bajars et al. |
| 3,914,332 A | 10/1975 | Dickason |

(Continued)

OTHER PUBLICATIONS

Kijima et al., A Chemical Potential Diagram and an In-situ X-ray Diffraction Analysis of a V-Mg-O Catalyst Used in the Oxidative Dehydrogenation of *n*-Butane, 2008, pp. 63-69.

(Continued)

*Primary Examiner* — Melvin C Mayes
*Assistant Examiner* — Colette Nguyen
(74) *Attorney, Agent, or Firm* — Harness, Dickey & Pierce, P.L.C.

(57) ABSTRACT

The present invention discloses a method of producing a magnesia-zirconia complex carrier for a catalyst for oxidative dehydrogenation of n-butane through a single-step precipitation process wherein the oxidative dehydrogenation of n-butane is to produce n-butene and 1,3-butadiene from n-butane; a method of producing a magnesium orthovanadate catalyst supported by thus prepared magnesia-zirconia complex carrier; and a method of producing n-butene and 1,3-butadiene using said catalyst.

3 Claims, 4 Drawing Sheets

(51) Int. Cl.
    *B01J 37/03*    (2006.01)
    *B01J 21/10*    (2006.01)
    *C07C 5/48*     (2006.01)
    *B01J 32/00*    (2006.01)
    *B01J 23/22*    (2006.01)
    *B01J 37/08*    (2006.01)
    *C07C 11/167*   (2006.01)

(56) References Cited

U.S. PATENT DOCUMENTS

| | | | |
|---|---|---|---|
| 6,187,984 B1 | 2/2001 | Wu et al. | |
| 6,433,241 B2 | 8/2002 | Wu et al. | |
| 2005/0228196 A1* | 10/2005 | Gaffney et al. | 562/547 |
| 2012/0232320 A1* | 9/2012 | Song et al. | 585/627 |

OTHER PUBLICATIONS

Marcu et al., Oxidehydrogenation of *n*-butane over tetravalent metal phosphates based catalysts, 2002, pp. 309-320.

Madeira et al., Electrical conductivity, basicity and catalytic activity of Cs-promoted α-NiMoO$_4$ catalysts for the oxidative dehydrogenation of *n*-butane, 1997, pp. 243-256.

Lemonidou et al., Investigations on the oxidative dehydrogenation of *n*-butane over VMgO-type catalysts, 1998, pp. 65-71.

Kung, Desirable Catalyst Properties in Selective Oxidation Reactions, vol. 25, No. 2, 1986, pp. 171-178.

Chaar et al., Selective Oxidative Dehydrogenation of Butane over V-Mg-O Catalysts, 1987, pp. 483-498.

Chaar et al., Selective Oxidative Dehydrogenation of Propane over V-Mg-O Catalysts, 1988, pp. 463-467.

Owen et al., Effect of cation reducibility on oxidative dehydrogenation of butane on orthovanadates, 1993, pp. 265-284.

Harlin et al., Alumina-Supported Vanadium Oxide in the Dehydrogenation of Butanes, 2000, pp. 67-78.

Murgia et al., Sol—gel synthesis of V$_2$O$_5$—SiO$_2$ catalyst in the oxidative dehydrogenation of *n*-butane, 2006, pp. 134-143.

Urlan et al., Oxidative dehydrogenation of *n*-butane over titanium pyrophosphate catalysts in the presence of carbon dioxide, 2008, pp. 2403-2406.

Armendariz et al., Oxidative dehydrogenation of n-butane on zinc-chromium ferrite catalysts, 1994, pp. 325-332.

Nieto et al., Oxidative dehydrogenation of *n*-butane on MgO-supported vanadium oxide catalysts, 1998, pp. 215-228.

Bhattacharyya et al., Oxidative dehydrogenation of n-butane to butadiene, 1992, pp. 29-43.

* cited by examiner

US 8,927,455 B2

SINGLE-STEP PRECIPITATION METHOD OF PRODUCING MAGNESIA-ZIRCONIA COMPLEX CARRIER FOR CATALYST FOR OXIDATIVE DEHYDROGENATION OF N-BUTANE, MAGNESIUM ORTHOVANADATE CATALYST SUPPORTED ON MAGNESIA-ZIRCONIA COMPLEX CARRIER, AND METHOD OF PRODUCING N-BUTENE AND 1,3-BUTADIENE USING SAID CATALYST

CROSS-REFERENCE TO RELATED APPLICATION

This application claims the benefit and priority of Korean Patent Application No. 10-2011-0101954, filed Oct. 6, 2011. The entire disclosure of the above application is incorporated herein by reference.

TECHNICAL FIELD

The present invention relates to a single-step precipitation method of producing a magnesia-zirconia complex carrier used for a catalyst for oxidative dehydrogenation of n-butane; a method of producing a magnesium orthovanadate (hereinafter, referred to as o-vanadate) catalyst supported by thus obtained magnesia-zirconia complex carrier, and a method of producing n-butene and 1,3-butadiene using said catalyst.

BACKGROUND OF THE INVENTION

Owing to the increasing demand for petrochemical products from developing countries such as China, in the recent petrochemical product market, the stable supply of olefins, particularly light olefins which are used as a raw material for various petrochemical products has become an issue in this market.

Among those light olefins, a demand for and value of N-butene and 1,3-butadiene which serve as a raw material for various synthetic rubber and copolymer products are particularly increasing, and the methods for producing them may be largely classified by naphtha cracking, direct dehydrogenation of n-butane or n-butene, or oxidative dehydrogenation of n-butane or n-butene. Among them, the naphtha cracking process affords most of n-butene and 1,3-butadiene supply in the market, reaching to approximately 90% of supply n-butene and 1,3-butadiene. However, a naphtha cracking process has a disadvantage such that it has a general purpose for producing basic petrochemical feedstock such as ethylene, propylene, etc., not a process dedicated to the production of n-butene and 1,3-butadiene. In the meantime, new establishment or expansion of naphtha cracking center only for the purpose of increasing the production of n-butene and 1,3-butadiene cannot be made without any particular plan, and if so, it would cause a further problem of surplus production of other basic petrochemical feedstock other than n-butene and 1,3-butadiene. Moreover, with an increasing demand for ethylene and propylene, new establishment and operation regarding a naphtha cracking process tends to be rather focused to increase in production yield of ethylene and propylene, and thus modified as a process using light hydrocarbons such as ethane, propane, etc. as a raw material which can result in high production yield for basic petrochemical feedstock such as ethylene, propylene and the like, although its yield for C4 mixtures is low. In addition to that, with the continuous price increase in raw materials for C4 production, the proportion of a process for obtaining C4 in the naphtha cracking process is relatively reduced. In consequence, with those obstacles as above, it is getting more difficult to secure C4 mixtures, particularly n-butene and 1,3-butadiene through a naphtha cracking process.

As the foregoing description, although n-butene and 1,3-butadiene supply majorly depend on a naphtha cracking process, this process cannot be an effective way to resolve the imbalance between supply and demand caused by recent increased demand in n-butene and 1,3-butadiene, based on the many reasons as above. In this circumstance, a dehydrogenation reaction in which hydrogens are removed from n-butane or n-butene thus obtaining n-butene and 1,3-butadiene, is recently getting a great attention as an alternative process which can rapidly cope with the increasing demand for n-butene and 1,3-butadiene in market, and thus other related studies have been vigorously made. [N. Kijima, M. Toba, Y. Yoshimura, Catal. Lett., vol. 127, p. 63 (2009); I. C. Marcu, I. Sandulescu, J. M. M. Millet, Appl. Catal. A, vol. 227, p. 309 (2002); L. M. Madeira, J. M. Herrmann, F. G. Freire, M. F. Portela, F. J. Maldonado, Appl. Catal. A, vol. 158, p. 243 (1997); A. A. Lemonidou, G. J. Tjatjopoulos, I. A. Vasalos, Catal. Today, vol. 45, p. 65 (1998)].

The dehydrogenation reaction of n-butane can be classified into direct dehydrogenation and oxidative dehydrogenation, wherein the direct dehydrogenation reaction of n-butane is highly exothermic and thus a thermodynamically disadvantageous reaction since hydrogen should be directly detached from n-butane as well as requires great energy consumption to satisfy the high-temperature reaction condition. For carrying out direct dehydrogenation, used are precious metal catalysts such as platinum or palladium, which require a reactivation process owing to their short lifetime in most cases, therefore the direct dehydrogenation is not considered to be a suitable commercial process for producing 1,3-butadiene. [A. Wu, C. A. Frake, U.S. Pat. No. 6,433,241 B2 (2002); A. Wu, C. A. Frake, U.S. Pat. No. 6,187,984 (2001)].

On the contrary, unlike the direct dehydrogenation, the oxidative dehydrogenation of n-butane, wherein n-butane and oxygen reacts to produce n-butene and water, and thus obtained n-butene further reacts with oxygen to produce 1,3-butadiene and water, is thermodynamically advantageous as compared to the direct dehydrogenation reaction of n-butane since an endothermic reaction turns to an exothermic reaction with the generation of water after the reaction, wherein water generated from the catalyst reaction may have a role of a heat sink which can prevent rapid temperature changes in the catalyst layer. In this respect, the oxidative dehydrogenation process of n-butane can be operated under process conditions more advantageous than those of the direct dehydrogenation process, and therefore, upon the development of a catalyst process for producing n-butene and 1,3-butadiene with high efficiency, this process can be a method which can cope with the recent increase in n-butane and 1,3-butadiene in the recent market.

As described above, the oxidative dehydrogenation of n-butane for producing n-butene and 1,3-butadiene includes a reaction between n-butane and oxygen to produce water and n-butene which reacts with oxygen in the same way again to produce water and 1,3-butadiene. From the above description, although this reaction has many advantages over the direct dehydrogenation of n-butane in many ways such as a thermodynamic aspect which makes possible to produce n-butene and 1,3-butadiene with a high yield, under mild reaction conditions, it has a drawback that many side reactions such as highly oxidative reactions which involve generation of carbon monoxide or carbon dioxide owing to the use of oxygen as a reactant.

Therefore, the most crucial technical point in the oxidative dehydrogenation process of n-butane is to achieve a catalyst with highly increased selectivity to n-butene and 1,3-butadiene by preventing side reactions such as complete-oxidative reactions, while achieving the conversion of n-butane to the maximum. Although the reaction mechanism of the oxidative dehydrogenation of n-butane has not yet been exactly known, it is reported that, as a first step, by the reaction of the active site of metal in the catalyst and lattice oxygen, hydrogen is detached from n-butane adsorbed in the solid catalyst and simultaneously a redox reaction of a catalyst itself and loss of lattice oxygen occur, and therefore complex oxide catalysts containing transition metal ions which may be in various oxidation states are essential to this oxidative dehydrogenation reaction [H. H. Kung, Ind. Eng. Chem. Prod. Res. Dev., vol. 25, p. 171 (1986)].

So far, catalysts known to effectively produce n-butene and 1,3-butadiene through oxidative dehydrogenation of n-butane are magnesium orthovanadate catalysts [M. A. Chaar, D. Partel, H. H. Kung, J. Catal., vol. 105, p. 483 (1987); M. A. Chaar, D. Partel, H. H. Kung, J. Catal., vol. 109, p. 463 (1988); O. S. Owen, H. H. Kung, J. Mol. Catal., vol. 79, p. 265 (1993); A. A. Lemonidou, G. J. Tjatjopoulos, I. A. Vasalos, Catal. Today, vol. 45, p. 65 (1998); Korean patent application No. 10-2011-0021037 (2011) [by Song In Kyu, Lee Ho Won, You Yoen Sik, Jo Young Jin, Lee Jin Suck, Jang Ho Sik; vanadium oxide catalysts [A. F. Dickason, U.S. Pat. No. 3,914,332 (1975); M. E. Harlin, V. M. Niemi, A. O. I. Krause, J. Catal. Vol. 195, p. 67 (2000); V. M. Murgia, E. M. F. Torres, J. C. Gottifredi, E. L. Sham, Appl. Catal. A, vol. 312, p. 134 (2006)]; pyrophosphate catalysts [I. C. Marcu, I. Sandulescu, J. M. M. Millet, Appl. Catal. A, vol. 227, p. 309 (2002); F. Urian, I. C. Marcu, I. Sandulescu, Catal. Commun., vol. 9, p. 2403 (2008)], ferrite catalysts [H. Armendariz, J. A. Toledo, G. Aguilar-Rios, M. A. Valenzuela, P. Salas, A. Cabral, H. Jimenez, I. Schifter, J. Mol. Catal., vol. 92, p. 325 (1994); L. Bajars, L. J. Croce, U.S. Pat. No. 3,303,234 (1967)] and the like.

The characteristic feature shared by the above complex oxide catalysts is the presence of transition metals, which are necessary for transition of electrons between the catalyst and n-butane via the redox reaction of the catalyst as explained above [H. H. Kung, Ind. Eng. Chem. Prod. Res. Dev., vol. 25, p. 171 (1986)]. The catalysts can carry out the oxidative dehydrogenation of n-butane by incorporating metals which can be oxidized and reduced such as, for example, vanadium, iron, nickel and titanium, etc., and among them, particularly, magnesium o-vanadate catalysts which contain vanadium are known to have high activity, based on which it is considered for the redox potential of vanadium metal to be suitable for the oxidative dehydrogenation of n-butane [M. A. Chaar, D. Partel, H. H. Kung, J. Catal., vol. 105, p. 483 (1987); M. A. Chaar, D. Partel, H. H. Kung, J. Catal., vol. 109, p. 463 (1988)].

Magnesium o-vanadate catalysts are generally produced to be the form in which the active phase of $Mg_3(VO_4)_2$ is supported by a separate metal oxide. It is reported that when magnesium o-vanadate catalysts are not supported, the activity is lower than that of supported magnesium o-vanadate.

For example, some results of oxidative dehydrogenation of n-butane by using unsupported magnesium o-vanadate catalysts have been reported in conventional patents and literatures, specifically, for example, 11.5% of n-butane conversion rate, 6.7% of dehydrogenation product yield under the conditions of 540° C. and the feed composition ratio of n-butane:oxygen:helium=4:8:88 [O. S. Owen, H. H. Kung, J. Mol. Catal., vol. 79, p. 265 (1993)], and 5.7% dehydrogenation product yield under the conditions of 540° C. and the feed composition ratio of n-butane:oxygen:helium=5:10:85 [A. A. Lemonidou, G. J. Tjatjopoulos, I. A. Vasalos, Catal. Today, vol. 45, p. 65 (1998)]. When magnesium o-vanadate catalysts are supported, the activity can be more improved [A. A. Lemonidou, G. J. Tjatjopoulos, I. A. Vasalos, Catal. Today, vol. 45, p. 65 (1998)]. Specifically, magnesia supported magnesium o-vanadate catalysts obtained by supporting vanadium to excessive amount of magnesia and their excellent activity for the oxidative dehydrogenation of n-butane have been reported [M. A. Chaar, D. Partel, H. H. Kung, J. Catal., vol. 109, p. 463 (1988); O. S. Owen, H. H. Kung, J. Mol. Catal., vol. 79, p. 265 (1993); A. A. Lemonidou, G. J. Tjatjopoulos, I. A. Vasalos, Catal. Today, vol. 45, p. 65 (1998)]. Specifically, it was reported that when the oxidative dehydrogenation of n-butane under the conditions of 600° C. and the composition ratio of n-butane:oxygen:nitrogen of 2:1:97 was conducted by using a magnesia-supported magnesium o-vanadate catalyst obtained by mixing magnesium hydroxide with a mixed aqueous solution of ammonium vanadate and ammonia with the ratio of Mg to V of 6:1, it resulted in 30.4% of n-butane conversion rate, 70.6% of dehydrogenation product selectivity and 21.5% of dehydrogenation product yield [N. Kijima, M. Toba, Y. Yoshimura, Catal. Lett., vol. 127, p. 63 (2009)], and when the oxidative dehydrogenation of n-butane under the conditions of 540° C. and the composition ratio of n-butane:oxygen:helium of 5:10:85 was conducted by using a magnesia-supported magnesium o-vanadate catalyst, it resulted in the yield of 22.8% [A. A. Lemonidou, G. J. Tjatjopoulos, I. A. Vasalos, Catal. Today, vol. 45, p. 65 (1998)]. Further, also reported were the results of 35.4% of n-butane conversion rate and 18.1% of dehydrogenation product yield, by using a magnesia-supported magnesium o-vanadate catalyst under the higher oxygen conditions wherein the composition ratio of n-butane:oxygen:helium=5:20:75, as compared to said reactions of the prior arts [J. M. Lopez Nieto, A. Dejoz, M. J. Vazquez, W. O'Leary, J. Cunningham, Catal. Today, vol. 40, p. 215 (1998)].

Further reported was a method for using magnesium o-vanadate catalyst which makes possible to increase the activity for the oxidative dehydrogenation of n-butane by mixing additives to magnesia-supported magnesium o-vanadate catalyst so as to obtain products from the dehydrogenation, n-butene and 1,3-butadiene with high yield in the literature of [D. Bhattacharyya, S. K. Bej, M. S. Rao, Appl. Catal. A, vol. 87, p. 29 (1992)], wherein the dehydrogenation was carried out under the conditions of 570° C., a composition ratio of n-butane:oxygen:nitrogen of 4:8:88 by using 25 wt % of a magnesia-supported magnesium o-vanadate catalyst further mixed with titanium oxide and chromium oxide, resulting in 54.0% of n-butane conversion rate and 33.8% of dehydrogenation product yield.

Although it is possible to the desired reaction product n-butene and 1,3-butadiene with a very high yield, by using said magnesia-supported magnesium o-vanadate catalyst in the oxidative dehydrogenation of n-butane, its commercial application is limited. This is because that although the magnesia-supported magnesium o-vanadate catalyst has high activity, the redox reaction of the catalyst which should be reversible is carried out partly irreversible, [N. Kijima, M. Toba, Y. Yoshimura, Catal. Lett., vol. 127, p. 63 (2009)], thereby failing to maintaining the high catalyst activity for a long time.

To solve such problem of said prior art, the present inventors established a method for producing a thermally- and chemically-stable magnesium o-vanadate catalyst supported by a zirconia or magnesia-zirconia complex carrier, without problems such as a decrease in catalyst activity with the lapse of time or low catalyst activity of other vanadium oxide catalysts, and also developed a catalyst reaction process for preparing n-butene and 1,3-butadiene at a high yield in a stable way by using thus prepared catalyst [by Song In Kyu, Lee Ho Won, You Yoen Sik, Jo Young Jin, Lee Jin Suck, Jang Ho Sik, Korean Patent application No. 10-2011-0021037 (2011); Song In Kyu, Lee Ho Won, You Yoen Sik, Jo Young Jin, Lee Jin Suck, Jang Ho Sik, Korean Patent application No. 10-2011-0051293 (2011)]. In the above-mentioned prior patent applications, the present inventors developed a method for preparing a magnesium o-vanadate catalyst supported by the magnesia-zirconia complex carrier which comprises magnesia and zirconia at a certain ratio, which can obtain n-butene and 1,3-butadiene at a high yield in a stable way through the oxidative dehydrogenation of n-butane without any hint of catalyst inactivation, in which the method comprises: preparing a zirconia carrier for a catalyst for the oxidative dehydrogenation of n-butane by a gel-oxalate method; then supporting magnesium and vanadium thereto, thus obtaining a zirconia carrier or a magnesia-zirconia complex carrier; and finally preparing a magnesium o-vanadate catalyst supported by the zirconia carrier or magnesia-zirconia complex carrier.

However, over the above-mentioned prior arts and patent applications, further improvement regarding the activity in the oxidative dehydrogenation of n-butane and the reproducibility of the catalyst preparation is still needed in this field of art.

SUMMARY OF THE INVENTION

In order to overcome the limitations of magnesium o-vanadate catalyst supported by magnesia reported in the prior arts including the patent applications of the present inventors, after persistent studies, the present inventors now achieved a method for preparing a magnesia-zirconia complex carrier, which makes possible to precisely adjust the ratio of the components in the magnesia-zirconia complex carrier to a certain ratio in an easy and simple way, by employing a single-step precipitation wherein magnesium and zirconium are precipitated at the same time, in a gel-oxalate method using oxalic acid and ethanol which is a commercial carrier for obtaining magnesia-zirconia used as a basic carrier of magnesium o-vanadate catalyst supported by the magnesia-zirconia complex carrier in an easy and cost-effective way as compared to the conventional sol-gel method.

Further, a method for preparing a catalyst which can easily produce a thermally- and chemically-stable catalyst with a high efficiency and an excellent reproducibility is provided according to present inventions, by preparing a magnesium o-vanadate catalyst supported by a magnesia-zirconia complex carrier wherein vanadium is supported to the magnesia-zirconia complex carrier prepared by the above-described magnesia-zirconia complex carrier preparation method through simple processes such as impregnation, drying and firing processes.

Further, by using a magnesium o-vanadate catalyst supported by the magnesia-zirconia complex carrier for a catalyst for oxidative dehydrogenation as prepared above, it is possible to produce n-butene and 1,3-butadiene with a high yield, thereby achieving the present invention.

It is possible to directly carry out an oxidative dehydrogenation reaction with the magnesium o-vanadate catalyst supported by the magnesia-zirconia prepared by the method according to the present invention, without a separate activation step at a high temperature at which the oxidative dehydrogenation is generally carried out. Further, since it uses a complex carrier consisting of magnesia and zirconia which is industrially widely used, it can be processed easily, thereby being directly applied to the process for preparing n-butene and 1,3-butadiene.

Therefore, one object of the present invention is to provide a method for producing a magnesia-zirconia complex carrier for a catalyst for oxidative dehydrogenation of n-butane in a simpler and reproducible way through a single-step, which is to support active elements comprised of magnesium o-vanadate and makes possible to prevent the magnesium o-vanadate activity from being decreased upon its application to the oxidative dehydrogenation of n-butane.

Another object of the present invention is to provide a method for producing a magnesium o-vanadate catalyst supported by a magnesia-zirconia complex carrier, which comprises the step of supporting the active component, i.e. magnesium o-vanadate to the magnesia-zirconia complex carrier prepared by the method for preparing a carrier for an oxidative dehydrogenation reaction of n-butane according to the present invention.

Still another object of the present invention is to provide a method for producing n-butene and 1,3-butadiene from n-butane by carrying out oxidative dehydrogenation of n-butane in a stable, simple and reproducible way with high activity, by specifically using a catalyst in which magnesium o-vanadate is supported to the magnesia-zirconia complex carrier prepared by the above method.

DETAILED DESCRIPTION OF THE INVENTION

In order to solve the above-described purposes, the present invention provides a method for preparing a magnesia-zirconia complex carrier for a catalyst for oxidative dehydrogenation of n-butane which comprises the following steps:
(a) preparing a magnesia-zirconia solid component by a single step gel-oxalate method, which comprises the synthesis of magnesia-zirconia by mixing an alcohol solution in which a magnesium precursor and a zirconium precursor are dissolved in an alcohol with another alcohol solution of oxalic acid in which oxalic acid is dissolved in an alcohol; and
(b) synthesizing magnesia-zirconia carrier for a catalyst for oxidative dehydrogenation of n-butane by separating, drying and heating the magnesia-zirconia solid component obtained from the above step (a).

As for the magnesium precursor and the zirconium precursor used in the above step (a), any conventionally used precursors may be used without limitation. However, for the magnesium precursor, at least one selected from magnesium chloride and magnesium nitrate may be preferably used; and as for the zirconium precursor, at least one selected from zirconium chloride, zirconium oxynitrate and zirconium oxychloride may be preferably used. Particularly among the above-listed, magnesium chloride and zirconium chloride are preferably used.

As for oxalic acid used in the above step (a), any commercially available products on the market may be used without limitation, and for example oxalic acid dihydrate may be preferably used.

As for the alcohols used in the above step (a), any alcohols which can dissolve the magnesium precursor and the zirconium precursor and oxalic acid, respectively may be used without limitation, and preferably used may be at least one alcohol selected from the group consisting of ethanol, propanol, butanol, 2-butanol, and particularly preferred is ethanol.

Although the amount (molar ratio) of oxalic acid required for converting the magnesium ions and zirconium ions dissolved in the alcohol in the above step (a) to magnesium oxalate and zirconium oxalate is theoretically, for magnesium, the same amount as magnesium, and for zirconium, twice of the amount of zirconium, in practice, it is preferred to use oxalic acid, for magnesium, at the amount more than twice of the amount of magnesium and for zirconium, at the amount more than 4 times of the amount of zirconium. This is because, in a solution in which magnesium ions and zirconium ions are mixed, for the method for preparing the magnesia-zirconia complex carrier through a single-step precipitation according to the present invention, conversion of the magnesium ions and zirconium ions to oxalate thereof respectively is not actively achieved. As the result, in order to convert all the amount of the magnesium ions and zirconium ions to magnesium oxalate and zirconium oxalate, said amount of oxalic acid is required, i.e. for magnesium, the amount more than twice of the amount of magnesium and, for zirconium, the amount more than 4 times of the amount of zirconium. In the meantime, unpredictable parameters such as solvent acidity owing to oxalic acid may become a problem, and thus the molar ratio of oxalic acid:magnesium=2-3:1 and of oxalic acid:zirconium=4-6:1, respectively is preferably used.

The method for mixing the mixed alcohol solution containing magnesium and zirconium with the alcohol solution of oxalic acid is not particularly limited, however it is preferred that the mixing of each solution is conducted as slowly as possible so that the oxalate particles of each metal can grow uniformly in its size, and the temperature of the mixed solution being stirred is preferably maintained at room temperature. For example, the alcohol solution of oxalic acid contained in a syringe can be injected to the mixed alcohol solution of magnesium and zirconium as slowly as possible, by using a syringe pump at the finely adjusted speed, for example 1-12 hours, preferably 3-6 hours at room temperature so that magnesia-zirconia synthesis can be sufficiently achieved.

The ratio of magnesia and zirconia in the above step (a) is not particularly limited, however, the molar ratio of zirconia:magnesia may be 0.5-16:1, preferably 0.5-4:1 for preparing a magnesia-zirconia complex carrier for a magnesium o-vanadate catalyst satisfying the purpose of the present invention, i.e. the activity of the catalyst can be stably maintained for a long time.

In the step (b), the solution from the step (a) which has been stirred for sufficient time is allowed to stand still for a period sufficient so that solid components can be precipitated, then it is subjected to a phase separation, for example by filtering so as to remove chloride ions, thereby obtaining magnesia-zirconia as a solid component sample.

In other words, the solid component may be obtained, for example, by separating the precipitated solid component and the alcohol from the solution obtained from the step (a) by filtering or centrifugation. Thus obtained solid component sample is dried, and heated, for example in an electric furnace at 350-800° C. and preferably 500-700° C. for 1-12 hours and preferably 3-6 hours so as to obtain a magnesia-zirconia carrier.

The purpose of drying the solid component sample is to remove the alcohol and moisture remained after the separation process of the sample. In this regard, the temperature by which alcohol evaporation is possible is determined as the lower limitation and the temperature by which thermal changes in the sample can be prevented may be determined as the upper limitation, and the time for drying may be limited within the range in which alcohol is expected to be completely removed from the sample. For example, the drying temperature may be determined to be 50-200° C. and preferably 70-120° C., and the drying time is 3-24 hours and preferably 6-12 hours.

The purpose of heating the dried solid component sample is not only to synthesize magnesia-zirconia from magnesia oxalate and zirconium oxalate but also to prevent catalyst denaturation during the use of the catalyst supported by the prepared carrier in the oxidative dehydrogenation reaction, taking the reaction temperature of oxidative dehydrogenation into consideration. For example, the heating process is preferably carried out in an electric furnace at 350-800° C. for 1-12 hours, when the heating temperature is less than 350° C. or the heating time is less than 1 hour, magnesia-zirconia is not sufficiently synthesized from magnesium oxalate and zirconium oxalate, and when the heating temperature is more than 800° C. or the heating time is more than 12 hours, the crystalline phase of zirconia in the magnesia-zirconia complex carrier is degenerated so that it might become unsuitable for the use as a carrier, disadvantageously.

A method for preparing a magnesium orthovanadate catalyst supported by the magnesia-zirconia complex carrier for the oxidative dehydrogenation of n-butane, wherein the magnesia-zirconia complex carrier is prepared as above described according to the present invention, comprising the following steps:

(i) impregnating the magnesia-zirconia complex carrier prepared as above with an aqueous vanadate solution; and (ii) drying and heating the product obtained from the above step (i), thereby obtaining a magnesium orthovanadate catalyst supported by the magnesia-zirconia complex carrier.

As for the vanadate used in the method for preparing a catalyst of the present invention, any vanadate conventionally used may be used without limitation, for example, ammonium metavanadate may be preferably used, however, without being limited to this, any other conventional vanadate may be further used depending on the purposes. When using ammonium metavanadate, the ammonium ions are removed during the impregnation, drying and heating processes, and thus it is possible to minimize the effect of ions. For this reason, ammonium vanadate is particularly preferred for the vanadate to be supported to the magnesia-zirconia complex carrier.

The aqueous vanadate solution may be prepared by dissolving vanadate into an aqueous oxalic acid solution or an ammonium hydroxide solution. Regarding the amount of water in the aqueous solution, the amount of water which can dissolve the salt may be enough, and preferably water is used at the minimum as long as it can sufficiently dissolve the salt. As for the aqueous oxalic acid or the ammonium hydroxide solution for helping the dissolution of vanadate, any commercially available products may be used without limitation, for example it is preferred to use oxalic acid dihydrate.

The purpose of drying in the above step (ii) is to remove the moisture remained after the impregnation with vanadate, therefore drying temperature and time may be limited according to drying conditions generally used to dry the moisture, for example the temperature may be 50-200° C., preferably 70-120° C. and the time may be 3-24 hours, preferably 6-12 hours.

The heating process in the above step (ii) which is to dissolve the vanadate, remove the oxalic acid used for impregnation and synthesize magnesium o-vanadate from the vandate supported in the magnesia-zirconia complex carrier, is carried out at 350-800° C., preferably at 500-700° C., for 1-12 hours, preferably for 1-6 hours, more preferably 3-6 hours. When the heating temperature is less than 350° C. and the heating time is less than 1 hour, magnesium o-vanadate is not sufficiently synthesized, and when the heating temperature is more than 800° C. or the heating time is more than 12 hours, there is a risk for zirconia to be degenerated, thereby being disadvantageous.

In order to overcome the drawbacks of the prior patent application of the present inventors[KR patent application No. 10-2011-0051293 (2011) by Song In Kyu, Lee Ho Won, You Yoen Sik, Jo Young Jin, Lee Jin Suck, Jang Ho Sik], that is a method for magnesium o-vanadate catalyst for oxidative dehydrogenation supported by a magnesia-zirconia complex carrier wherein magnesia and zirconia is mixed at a specific ratio, the magnesia-zirconia supported magnesium o-vanadate catalyst of the present invention prepared as above can provide the most suitable magnesia-zirconia complex carrier in easier and simpler way by using a single-step precipitation method for synthesizing the magnesia and zirconia at the same time in which the optimal mixing ratio of magnesia and zirconia can be further easily and precisely adjusted.

This is because, the synthesis of magnesia-zirconia in the method for preparing a carrier according to the present invention is carried out by a single step, as compared to the prior patent wherein magnesia-zirconia was obtained through two synthetic processes. The method using a single step synthesis according to the present invention has advantages such that the process is simple and the most suitable magnesia-zirconia complex carrier having more uniform characteristics in the resulted magnesia-zirconia can be obtained. The magnesia-zirconia complex carrier obtained by the method according to the present invention has no problem in its processability like the magnesia-zirconia of the prior patent application; and it can be directly applied to oxidative dehydrogenation of n-butane without requiring a separate activation step under the reaction conditions, thereby being directly applied to commercial processes.

Further, the present invention provides a method for preparing n-butene and 1,3-butadiene by oxidative dehydrogenation of n-butane on the magnesium o-vanadate supported by the magnesia-zirconia complex carrier prepared by the method as described above.

The reactant for the oxidative dehydrogenation of n-butane is a mixed gas comprising n-butane, oxygen and nitrogen, at the ratio by volume of n-butane:oxygen:nitrogen=2-10:0.5-40:50-97.5, preferably n-butane:oxygen:nitrogen=4:2-20:76-94, more preferably 4:2-10:86-94. When the volume ratio of n-butane, oxygen and nitrogen is out of said range, a side reaction, i.e. complete oxidation during the oxidative dehydrogenation of n-butane occurs greatly; the catalyst activity becomes lowered and process safety is not good, disadvantageously.

When feeding the reactant in the form of a mixed gas to a reactor, the amount of the reactant being fed which may be adjusted by a mass flow meter controller is adjusted to be preferably 50-5000 h$^{-1}$, preferably 500-3000 h$^{-1}$, more preferably 1000-2000 h$^{-1}$ of Gas hourly space velocity (GHSV) based on the amount of n-butane. When the space velocity is less than 50 h$^{-1}$, the catalyst reaction is localized to a limited section, leading to coking of the side products from the catalyst reaction, or heat emitted during the reaction may cause a hot spot, disadvantageously, and when the speed is more than 5000 h$^{-1}$, the catalyst reaction cannot sufficiently occur in the reactant passing the catalyst bed, disadvantageously.

The temperature for carrying out the oxidative dehydrogenation of n-butane is preferably maintained at the range of 300-800° C., more preferably 450-600° C., and most preferably 500° C. When the reaction temperature is less than 300° C., n-butane cannot be sufficiently activated, and when it is more than 800° C., decomposition reaction of n-butane occurs, disadvantageously.

INDUSTRIAL AVAILABILITY

According to the present invention, it is possible to easily produce a magnesia-zirconia complex carrier comprising magnesia and zirconia at optimal ratio through a simple single-step synthetic route, and to ensure the excellent reproducibility in carrier preparation.

Further, since the catalyst preparation process of supporting vanadium to the resulted carrier is also carried out by a simple method, it is also possible to ensure the reproducibility in preparing a magnesium o-vanadate catalyst supported by the magnesia-zirconia complex carrier. Therefore, it becomes possible to obtain a magnesium o-vanadate catalyst based on the magnesia-zirconia complex carrier for oxidative dehydrogenation of n-butane which can produce n-butene and 1,3-butadiene with a high yield in a stable way. Moreover, the specific gravity of the resulted catalyst prepared by the method according to the present invention is lower than that of the magnesium o-vanadate supported by the magnesia-zirconia complex carrier prepared according to prior art [Korean Patent application No. 10-2011-0051293 (2011) by Song In Kyu, Lee Ho Won, You Yoen Sik, Jo Young Jin, Lee Jin Suck and Jang Ho Sik], therefore even if a smaller amount of catalyst is applied to the same process, it is possible to obtain even higher activity, thereby being very cost-effective.

Further, according to the present invention, n-butene and 1,3-butadiene for which demand and value are gradually increasing owing to their wide use as intermediates for various petrochemical products in petrochemical industry can be prepared from n-butane which does not have wide applications, thereby being possible to achieve highly added value of C4 petrochemical feedstocks. Additionally, by the present invention, it is possible to ensure a process dedicated to the production of n-butene and 1,3-butadiene without new establishment of additional naphtha crackers, thereby satisfying demand for n-butene and 1,3-butadiene and acquiring economic benefits while actively coping with the market changes in the future.

EMBODIMENTS TO CARRY OUT THE INVENTION

Figure 1:
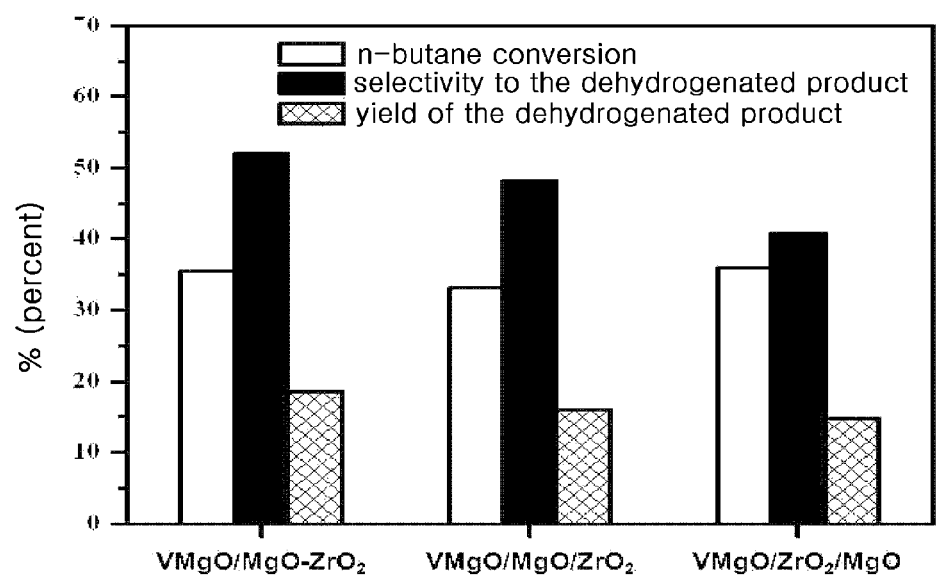
FIG. 1 is a plot representing the differences in catalyst activities over oxidative dehydrogenation of n-butane between 3 different species of magnesium o-vanadate catalysts supported by magnesia-zirconia prepared by the example 1, the comparative examples 2 and 3, after carrying out an oxidative dehydrogenation reaction for 12 hours.

Hereinafter, the present invention is further illustrated in detail via specific examples as given below. However, it should be understood that the following examples are described only for an illustrative purpose, without any intention to limit the scope of the present invention.

[Carrier Preparation Example]

Preparation of Magnesia-Zirconia Complex Carrier (MgO—ZrO2) by a Single-Step Gel-Oxalate Precipitation Method The present example is to obtain 5 g of a magnesia-zirconia complex carrier wherein the molar ratio of magnesia:zirconia=4:1 through a single-step gel-oxalate precipitation method according to the present invention.

Magnesium chloride 6.7 g and zirconium chloride 4.1 g were dissolved into ethanol (500 ml) so as to prepare a mixed ethanol solution of magnesium and zirconium, and oxalic acid dihydrate 26.6 g was dissolved into ethanol (200 ml) so as to prepare an ethanol solution of oxalic acid. After dissolution is sufficiently achieved in each solution, the ethanol solution of oxalic acid was injected to the mixed ethanol solution of magnesium and zirconium by using a syringe pump as slowly as possible, and the mixture was sufficiently stirred. Thus obtained mixed solution was again stirred at room temperature for 3 hours by using a magnetic stirrer for sufficient agitation, and allowed to stand still at room temperature for 12 hours for the subsequent phase separation. In order to remove unnecessary ions such as chloride from the phase-separated mixed solution, the ethanol solution was filtered and the filtered material was again washed with the ethanol solution and stirred, and this same procedure was conducted several times. Then, the final solution having precipitates was centrifuged and thus obtained solid sample was dried at 80° C. for 12 hours. Thus prepared solid sample was heated in an electric furnace maintained at 550° C. for 3 hours, thereby obtaining a magnesia-zirconia prepared by a single-step gel-oxalate method.

[Comparative Carrier Preparation Example 1]

Preparation of Magnesia-Zirconia Complex Carrier (MgO—$ZrO_2$) by a Single-Step Gel-Oxalate Precipitation Method In order to compare with the magnesia-zirconia complex carrier prepared by the above method as in carrier preparation example according to the present invention, a comparative magnesia-zirconia complex carrier on a zirconia basis (MgO/$ZrO_2$) prepared via a 2-step gel-oxalate method was produced according to Korean Patent application No. 10-2011-0051293 (2011)[by Song In Kyu, Lee Ho Won, You Yoen Sik, Jo Young Jin, Lee Jin Suck and Jang Ho Sik] and the preparation method in detail is as follows.

For preparing 2.2 g of zirconia, zirconium chloride 4.1 g was dissolved into ethanol (220 ml) so as to prepare an ethanol solution of zirconium, and oxalic acid dihydrate 4.4 g was dissolved into ethanol (45 ml) so as to prepare an ethanol solution of oxalic acid. After dissolution is sufficiently achieved in each solution, the ethanol solution of oxalic acid was injected to the ethanol solution of zirconium by using a syringe pump as slowly as possible, and the mixture was sufficiently stirred. Thus obtained mixed solution was subjected to a single phase gel-oxalate method using filtration, drying and heating processes as same as described in the above Carrier preparation example so as to prepare zirconia.

To the prepared zirconia, 18.0 g magnesium nitrate 6 hydrates dissolved in a small amount of distilled water was mixed by a general initial impregnation, and then the zirconia sample supported by magnesium was dried at 80° C. for 12 hours. The resulted solid sample was heated in an electric furnace under air atmosphere maintained at 550° C. for 3 hours so that magnesia was formed from the magnesium salt, resulting in a magnesia-zirconia complex carrier on a zirconia basis wherein the molar ratio of magnesia:zirconia was 4:1.

[Comparative Carrier Preparation Example 2]

Preparation of Magnesia-Zirconia Complex Carrier on a Zirconia Basis (MgO—$ZrO_2$) Prepared by a Gel-Oxalate Precipitation Method In order to compare with the magnesia-zirconia complex carrier prepared by the above Carrier preparation example according to the present invention, a comparative magnesia-zirconia complex carrier on a magnesia basis ($ZrO_2$)/MgO) prepared via a 2-step gel-oxalate method was produced and the preparation method in detail is as follows.

For preparing 2.8 g of magnesia, magnesium chloride 6.7 g was dissolved into ethanol (280 ml) so as to prepare an ethanol solution of magnesium, and oxalic acid dihydrate 17.7 g was dissolved into ethanol (150 ml) so as to prepare an ethanol solution of oxalic acid. After dissolution is sufficiently achieved in each solution, the ethanol solution of oxalic acid was injected to the ethanol solution of magnesium by using a syringe pump as slowly as possible, and the mixture was sufficiently stirred. Thus obtained mixed solution was subjected to a single phase gel-oxalate method using filtration, drying and heating processes as same as described in the above Carrier preparation example so as to prepare magnesia.

To the prepared magnesia, 4.1 g zirconium oxynitrate hydrate dissolved in a small amount of distilled water was mixed by a general initial impregnation, and then the magnesia sample supported by zirconium was dried at 80° C. for 12 hours. The resulted solid sample was heated in an electric furnace under air atmosphere maintained at 550° C. for 3 hours so that zirconia was formed from the zirconium salt, resulting in a magnesia-zirconia complex carrier on a magnesia basis wherein the molar ratio of magnesia:zirconia was 4:1.

[Catalyst Preparation Example 1]

Preparation of a Magnesium O-Vanadate Catalyst Supported by the Magnesia-Zirconia Complex Carrier by Supporting Said Carrier to Vanadate For supporting vanadium to 3 g of the magnesia-zirconia sample obtained from Carrier preparation example as above to the content of 9.0 wt %, ammonium vanadate 0.74 g was dissolved into and impregnated with an aqueous solution of oxalic acid comprising oxalic acid 1.6 g dissolved therein. The resulted solution was dried at 80° C. for 12 hours, thereby obtaining a solid sample. The obtained solid sample was heated in an electric furnace under air atmosphere maintained at 550° C. for 3 hours, resulting in a magnesia o-vanadate catalyst supported by the magnesia-zirconia complex carrier.

The catalyst prepared by the above process according to the present invention was referred as VMgO/MgO—$ZrO_2$ that is a catalyst supported by the magnesia-zirconia complex carrier prepared by a single-step gel-oxalate method for a magnesia-zirconia complex carrier synthesis.

[Catalyst Preparation Examples 2-5]

Preparation of 5 Different Magnesium O-Vanadate Catalysts Supported by Magnesia-Zirconia Complex Carriers (MgO—$ZrO_2$) by Varying the Content of Vanadium Supported Thereto, Wherein the Carriers were Prepared by the Single-Step Gel-Oxalate Method By varying the content of vanadium to be supported to the magnesia-zirconia complex carrier prepared by Example of carrier preparation according to the present invention as above, total 5 species of magnesium o-vanadate catalyst were prepared including the above-described Example of carrier preparation and Example of catalyst preparation.

Specifically, the amount of vanadium to be supported was adjusted to 2.8 wt % (Catalyst preparation example 2), 4.2 wt % (Catalyst preparation example 3), 5.6 wt % (Catalyst preparation example 4) and 11.2 wt % (Catalyst preparation example 5), respectively, by varying the concentration of the aqueous solution of vanadium oxalic acid, thereby preparing 5 different magnesium o-vanadate catalysts supported by a magnesia-zirconia complex carrier. Each catalyst was referred as X—VMgO/MgO—ZrO$_2$ (X=vanadium content) depending on the vanadium content.

[Comparative Catalyst Preparation Example]

For supporting vanadium to 3 g of each magnesia-zirconia sample obtained from Comparative carrier preparation examples 1 and 2 as above to the content of 9.0 wt %, ammonium vanadate 0.74 g was dissolved into and impregnated with an aqueous solution of oxalic acid comprising oxalic acid 1.6 g dissolved therein. The resulted solution was dried at 80° C. for 12 hours, thereby obtaining a solid sample. The obtained solid sample was heated in an electric furnace under air atmosphere maintained at 550° C. for 3 hours, resulting in two species of magnesium o-vanadate catalysts supported by the magnesia-zirconia complex carrier, respectively.

For the catalyst supported by a magnesia-zirconia complex carrier according to Comparative carrier preparation example 1 wherein the carrier was prepared by supporting magnesium salt on zirconia prepared by a gel-oxalate method for a magnesia-zirconium complex carrier synthesis, was referred as VMgO/MgO/ZrO$_2$; for the catalyst supported by a magnesia-zirconia complex carrier according to Comparative carrier preparation example 2 wherein the carrier was prepared by supporting zirconium salt on magnesia prepared by a gel-oxalate method for a magnesia-zirconium complex carrier synthesis, was referred as VMgO/ZrO$_2$/MgO.

EXAMPLE 1

Oxidative Dehydrogenation of N-Butane by Using Continuous Flow Type Catalyst Reactor The oxidative dehydrogenation of n-butane was carried out by using the magnesium o-vanadate catalyst supported by the magnesia-zirconia complex carrier, prepared according to the above Carrier preparation example and Catalyst preparation example under the conditions as described below.

The reactant for the oxidative dehydrogenation of n-butane in this example 1 was a C4 mixture containing 99.4 wt % of n-butane, and the specific composition thereof was represented in the following table 1.

TABLE 1

| Composition | Molecular formula | Wt % |
|---|---|---|
| i-butane | C$_4$H$_{10}$ | 0.18 |
| n-butane | C$_4$H$_{10}$ | 99.40 |
| I-butene | C$_4$H$_8$ | 0.34 |
| cis-2-butene | C$_4$H$_8$ | 0.08 |
| Total | | 100.00 |

The C4 mixture as a reactant was fed in the form of a mixed gas with oxygen and nitrogen. The composition ratio of the reactant was determined based on the amount of n-butane in the C4 mixture, to be n-butane:oxygen:nitrogen of 4:8:88 by volume.

The oxidative dehydration reaction was carried out by fixing the catalyst powder in a linear shaped quartz reactor for the catalyst reaction, maintaining the reaction temperature of the catalyst bed by placing the reactor in an electric furnace, and letting the reactant continuously passed the catalyst bed inside the reactor thereby proceeding with the reaction.

The amount of catalyst was set to achieve the feeding speed of the reactant to be 2000 h$^{-1}$ based on n-butane. Before flowing the reactant, while flowing nitrogen and oxygen, the temperature of the reactor with the fixed bed was raised from the room temperature to 500° C. for catalyst activation, and then the reaction temperature, i.e. the temperature of the catalyst bed of the fixed bed reactor was maintained at 500° C., while flowing the reactant, i.e. n-butane, so as to carry out the reaction. Since the product obtained from the reaction contained carbon dioxide caused from complete oxidation, side products from cracking, other side products for example from an isomerization reaction and unreacted n-butane, other than the main products n-butene and 1,3-butadiene, gas chromatography was used to separate and analyze them. The n-butane conversion rate, the selectivity to dehydrogenation products and yield of the oxidative dehydrogenation of n-butane carried out on the magnesium o-vanadate catalyst supported by the magnesia-zirconia complex carrier prepared by the single-step gel-oxalate method were calculated by the following equation 1, 2 and 3.

$$\text{conversion rate (\%)} = \frac{\text{mole number of reacted } n\text{-butane}}{\text{mole number of fed } n\text{-butane}} \times 100 \quad [\text{Equation 1}]$$

$$\text{selectivity (\%)} = \frac{\text{mole number of the resulted dehydrogenation product}}{\text{mole number of the reacted } n\text{-butane}} \times 100 \quad [\text{Equation 2}]$$

$$\text{Yield (\%)} = \frac{\text{mole number of the resulted dehydrogenation product}}{\text{mole number of fed } n\text{-butane}} \times 100 \quad [\text{Equation 3}]$$

The oxidative dehydrogenation of n-butane was carried out, for 12 hours, on the magnesium o-vanadate catalyst supported by the magnesia-zirconia complex carrier prepared by the single-step gel-oxalate method of Carrier preparation example and Catalyst preparation example 1 as above according to the present invention. At 12 hours after start of the reaction, the test results (catalyst activity) were represented in the following Table 2 and FIG. 1.

TABLE 2

| Catalyst | n-butane conversion rate(%) | Selectivity to products in dehydrogenation(%) | Product yield in dehydrogenation(%) |
|---|---|---|---|
| VMgO/ MgO—ZrO$_2$ | 35.6 | 52.1 | 18.5 |

COMPARATIVE EXAMPLE 1

Activity of the Magnesium O-Vanadate Catalyst Supported by Magnesia-Zirconia Complex Carrier on the Basis of Zirconia Prepared by a Gel-Oxalate Method According to Comparative Carrier Preparation Example 1 (VMgO/MgO/ZrO2), in an Oxidative Dehydrogenation Reaction For comparing the oxidative dehydrogenation activity, with the magnesium o-vanadate catalyst supported by the magnesia-zirconia complex carrier prepared by the single-step gel-oxalate method according to Example 1, the oxidative dehydrogenation of n-butane was carried out as in the method described in Example 1, except that a magnesium o-vanadate catalyst supported by the magnesia-zirconia complex carrier on the basis of zirconia prepared by the conventional gel-oxalate method reported in the prior patent application of the present inventors according to Comparative carrier preparation example 1 and Comparative catalyst preparation example was used instead of the catalyst of Example 1.

The test results of this Comparative example 1 were represented in the following Table 3 and FIGS. 1 and 2. The results shown in Table 3 and FIG. 1 were obtained after carrying out an oxidative dehydrogenation reaction of n-butane for 12 hours by using a magnesium o-vanadate catalyst supported by a magnesia-zirconia complex carrier on the basis of zirconia (VMgO/MgO/$ZrO_2$), and the results shown in FIG. 2 represented the activity changes over 12 hours.

TABLE 3

| Catalyst | n-butane conversion rate(%) | Selectivity to products in dehydrogenation (%) | Product yield in dehydrogenation (%) |
|---|---|---|---|
| VMgO/MgO/$ZrO_2$ | 33.2 | 48.2 | 16.0 |

COMPARATIVE EXAMPLE 2

Activity of the Magnesium O-Vanadate Catalyst Supported by Magnesia-Zirconia Complex Carrier on the Basis of Magnesia Prepared by a Gel-Oxalate Method (VMgO/$ZrO_2$/MgO), in an Oxidative Dehydrogenation Reaction For comparing the oxidative dehydrogenation activity, with the magnesium o-vanadate catalyst supported by the magnesia-zirconia complex carrier prepared according to Example 1 and the magnesium o-vanadate catalyst supported by the magnesia-zirconia complex carrier on the basis of zirconia according to comparative example 1, the oxidative dehydrogenation of n-butane was carried out as in the method described in Example 1, except that a magnesium o-vanadate catalyst supported by the magnesia-zirconia complex carrier on the basis of magnesia prepared according to Comparative carrier preparation example 2 and Comparative catalyst preparation example was used instead of the catalyst of Example 1.

The test results of this Comparative example 2 were represented in the following Table 4 and FIGS. 1 and 2. The results shown in Table 4 and FIG. 1 were obtained after carrying out an oxidative dehydrogenation reaction of n-butane for 12 hours by using a magnesium o-vanadate catalyst supported by a magnesia-zirconia complex carrier on the basis of magnesia (VMgO/$ZrO_2$/MgO), and the results shown in FIG. 2 represented the changes in catalyst activity to the oxidative dehydrogenation reaction over 12 hours.

TABLE 4

| Catalyst | n-butane conversion rate(%) | Selectivity to products in dehydrogenation(%) | Products yield in dehydrogenation (%) |
|---|---|---|---|
| VMgO/$ZrO_2$/MgO | 36.0 | 40.9 | 14.7 |

When the magnesium o-vanadate catalyst supported by the magnesium-zirconia complex carrier prepared through a single-step according to the present invention and the magnesium o-vanadate catalyst supported by the magnesium-zirconia complex carrier based on zirconia or magnesia prepared through a series of 2-steps are used in an oxidative dehydrogenation reaction, the effect of each complex carrier of the magnesium o-vanadate on the reaction activity were investigated. In this regard, the test results of the example 1 and comparative examples 1 and 2 were compared with each other, wherein the oxidative dehydrogenation reaction of n-butane was carried out for 12 hours and summarized in the following Table 5 and FIGS. 1 and 2.

TABLE 5

| Catalyst | n-butane conversion rate(%) | Selectivity to products in dehydrogenation(%) | Product yield in dehydrogenation (%) |
|---|---|---|---|
| Example 1(VMgO/MgO—$ZrO_2$) | 35.6 | 52.1 | 18.5 |
| Comparative example 1(VMgO/MgO/$ZrO_2$) | 33.2 | 48.2 | 16.0 |
| Comparative example 2(VMgO/$ZrO_2$/MgO) | 36.0 | 40.9 | 14.7 |

Figure 2:
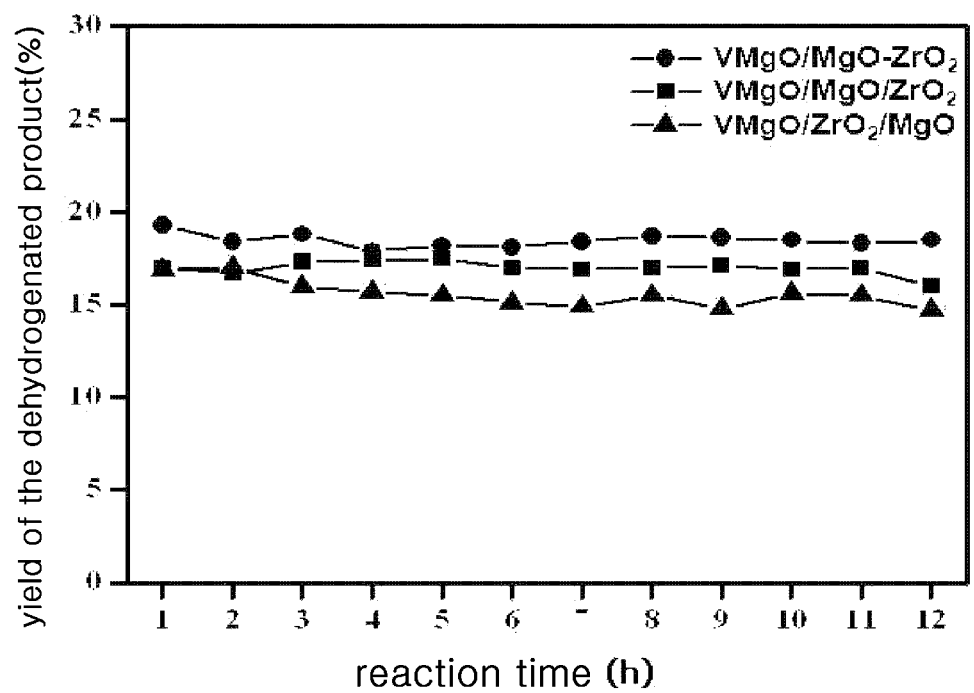
FIG. 2 is a plot representing the catalyst activity changes over time and differences thereof in an oxidative dehydrogenation reaction of n-butane between the 3 different species of magnesium o-vanadate catalysts supported by a magnesia-zirconia complex carrier of the example 1 and comparative examples 1 and 2.

As seen from Table 5 and FIG. 1, in the test for catalyst activity, the magnesium o-vanadate catalyst supported by magnesia-zirconia complex carrier prepared by the single-step according to Examples of the present invention showed higher catalyst activity showed higher activity and particularly excellent selectivity for dehydrogenation products from dehydrogenation of n-butene and 1,3-butadiene as compared to the magnesium o-vanadate catalysts based on a magnesia-zirconia complex carrier prepared according to Comparative examples 1 and 2.

Based on the above results, the magnesia-zirconia complex carrier prepared by the single-step gel-oxalate method according to the present invention was considered to be most suitable for a carrier for a catalyst for oxidative dehydrogenation of n-butane, and therefore it is possible to anticipate higher catalyst activity as compared to the magnesium o-vanadate supported by a magnesia-zirconia complex carrier prepared by a two-step synthesis method based on zirconia according to prior arts.

In FIG. 2, the catalyst activity changes over time for 3 different species of magnesium o-vanadate catalysts supported by a magnesia-zirconia complex carrier in an oxidative dehydrogenation reaction of n-butane were represented. In all the 3 catalysts based on 3 different complex carriers, noticeable catalyst inactivation was not observed, and therefore the 3 species of catalysts were considered to be thermally and chemically stable to oxidative dehydrogenation of n-butane.

EXAMPLE 2

Activity of a Magnesium O-Vanadate Catalyst (X—VMgO/MgO—ZrO$_2$, X=V content) to an Oxidative Dehydrogenation Reaction Wherein the Catalyst is Based on a Magnesia-Zirconia Prepared by a Single-Step Gel-Oxalate Method and has Various Vanadium Content An oxidative dehydrogenation reaction of n-butane was carried out as in the method described in Example 1 except that magnesium o-vanadate catalysts supported by magnesia-zirconia complex carrier prepared by a single-step gel-oxalate method according to Carrier preparation example and Catalyst preparation example with various vanadium contents were used. The test results of this Example 2 were represented in the following Table 6 and FIG. 3, as the catalyst activity changes over time regarding oxidative dehydrogenation of n-butane.

TABLE 6

| | Yield of dehydrogenation product (%) | | | | | |
|---|---|---|---|---|---|---|
| | time (h) | | | | | |
| catalyst | 1 | 2 | 3 | 4 | 5 | 6 |
| Catalyst preparation example 2 (2.8-VMgO/MgO—ZrO$_2$) | 11.8 | 12.1 | 12.3 | 11.8 | 12.4 | 12.6 |
| Catalyst preparation example 3 (4.2-VMgO/MgO—ZrO$_2$) | 19.4 | 19.5 | 18.6 | 18.1 | 19.0 | 18.4 |
| Catalyst preparation example 4 (5.6-VMgO/MgO—ZrO$_2$) | 20.9 | 20.1 | 19.9 | 19.7 | 19.5 | 19.8 |
| Catalyst preparation example 1 (9.0-VMgO/MgO—ZrO$_2$) | 19.3 | 18.4 | 18.8 | 17.9 | 18.2 | 18.2 |
| Catalyst preparation example 5 (11.2-VMgO/MgO—ZrO$_2$) | 13.8 | 14.2 | 14.4 | 14.3 | 14.5 | 14.6 |

Figure 3:
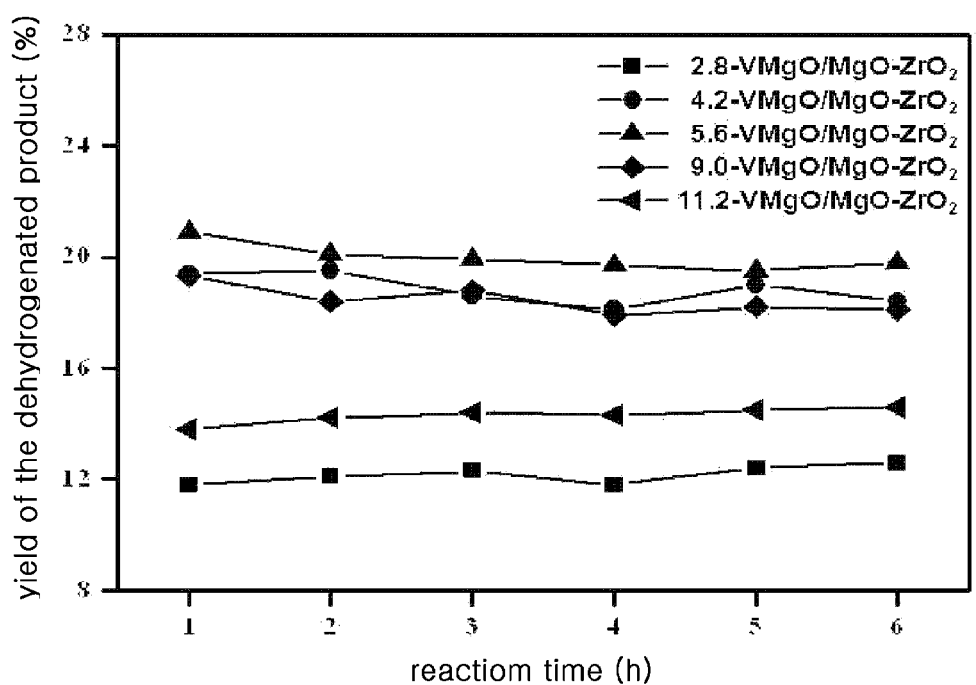
FIG. 3 is a plot representing the catalyst activity changes over time and differences thereof in oxidative dehydrogenation of n-butane between 5 different magnesium o-vanadate catalysts supported by the magnesia-zirconia complex carriers, wherein the amount of vanadium supported in the catalysts is different from each other according to the example 2 of the present invention.

As seen from Table 6 and FIG. 3, in the catalyst activity test, for a magnesium o-vanadate catalyst supported by the magnesia-zirconia complex carrier, the catalyst activity was different depending on each catalyst having different vanadium contents. However, all of 5 catalysts showed stable oxidation dehydrogenation of n-butane for 6 hours. From this fact, it can be known that although the vanadium content becomes different, the catalyst stability does not change much. Therefore, now it is possible to design magnesium o-vanadate catalyst supported by magnesia-zirconia complex carrier having a high reaction activity without any deterioration in the catalyst stability regarding the oxidative dehydrogenation reaction by varying the vanadium content. Accordingly, it is possible to prepare a catalyst having optimal reactivity by adjusting the amount of vanadium being supported to the catalyst.

For investigating the optimum vanadium content in a magnesium o-vanadate supported by a magnesia-zirconia complex carrier, after the 6 hour's oxidative dehydrogenation reaction in this Example 2, the catalyst activity was represented in the following Table 7 and FIG. 4.

TABLE 7

| Catalyst | n-butane conversion rate(%) | Selectivity to products in dehydrogenation (%) | Product yield in dehydrogenation (%) |
|---|---|---|---|
| Catalyst preparation example 2 (2.8-VMgO/MgO—ZrO$_2$) | 12.7 | 52.1 | 7.2 |
| Catalyst preparation example 3 (4.2-VMgO/MgO—ZrO$_2$) | 45.5 | 40.4 | 18.4 |
| Catalyst preparation example 4 (5.6-VMgO/MgO—ZrO$_2$) | 44.2 | 44.8 | 19.8 |
| Catalyst preparation example 1 (9.0-VMgO/MgO—ZrO$_2$) | 33.5 | 54.4 | 18.2 |
| Catalyst preparation example 5 (11.2-VMgO/MgO—ZrO$_2$) | 27.4 | 53.1 | 14.6 |

Figure 4:
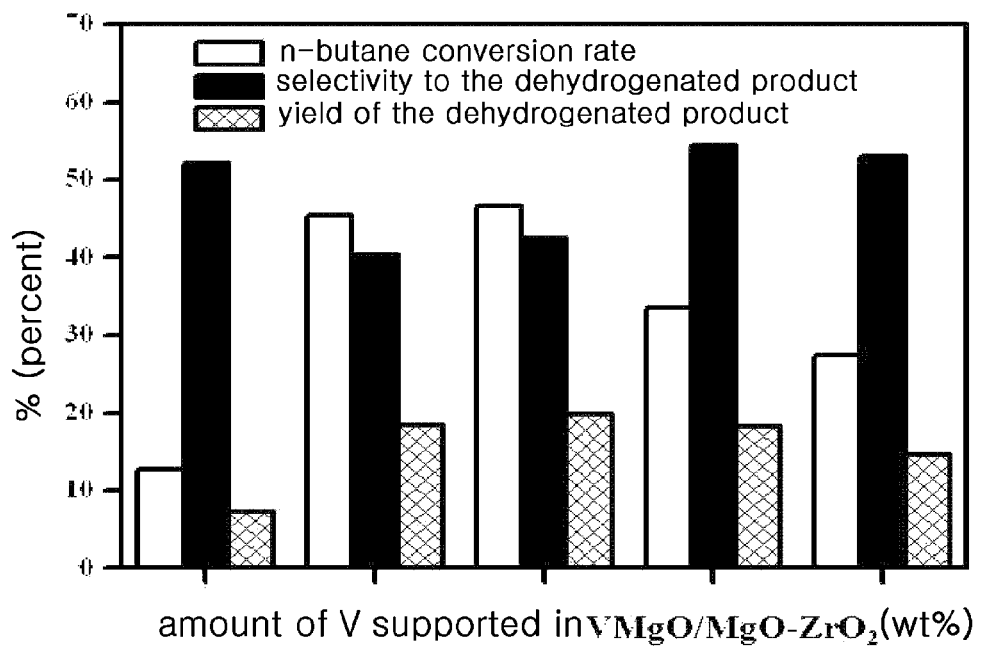
FIG. 4 is a plot representing the differences in catalyst activities over oxidative dehydrogenation of n-butane between different magnesium o-vanadate catalysts supported by 5 magnesia-zirconia complex carriers wherein the amount of vanadium supported in the catalysts is different from each other according to the example 2 of the present invention, after carrying out an oxidative dehydrogenation reaction for 12 hours.

As seen from Table 7 and FIG. 4, in the oxidative dehydrogenation reaction of n-butane by magnesium o-vanadate catalysts supported by a magnesia-zirconia complex carrier having different vanadium contents, depending on the vanadium content supported in the catalyst, the conversion rate of n-butane was increased for a while and then decreased i.e. showing a "volcano" curve; and the selectivity to the products from the dehydrogenation reaction decreased for a while and then increased again. As seen from FIG. 4, the vanadium content being supported to a catalyst has greater effect on the conversion rate than other parameters, and consequently the yield for the products from the dehydrogenation reaction showed a "volcano" curve as in the conversion rate of n-butane. Therefore, the catalyst 5.6-VMgO/MgO—ZrO$_2$ of which supported vanadium content was 5.6 wt % showed the highest reaction activity. Therefore, it can be seen that the catalyst being capable of providing the products from the dehydrogenation reaction at the greatest amount was 5.6-VMgO/MgO—ZrO$_2$ catalyst, of which supported vanadium content was 5.6 wt %.

The invention claimed is:

1. A method for preparing a magnesia-zirconia complex carrier for a catalyst for oxidative dehydrogenation of n-butane which comprises the following steps:
    (a) preparing a magnesia-zirconia solid component by a single step gel-oxalate method, which comprises the synthesis of magnesia-zirconia by mixing an alcohol solution in which a magnesium precursor and a zirconium precursor are dissolved in an alcohol with an alcohol solution of oxalic acid in which oxalic acid is dissolved in an alcohol; and
    (b) obtaining a magnesia-zirconia carrier for a catalyst for oxidative dehydrogenation of n-butane by separating, drying and heating the magnesia-zirconia solid component obtained from the above step (a).

2. The method according to claim 1, wherein, in the above step (b), drying is carried out at 50-200° C. for 3-24 hours, and heating is carried out at 350-800° C. for 1-12 hours.

3. The method according to claim 1, wherein the alcohol is at least one selected from the group consisting of ethanol, propanol, butanol and 2-butanol.

* * * * *